US006541433B2

(12) United States Patent
Schultz et al.

(10) Patent No.: US 6,541,433 B2
(45) **Date of Patent: *Apr. 1, 2003**

(54) SHAPED SOAP PRODUCT COMPRISING TALC, ONE OR MORE FATTY ACIDS IN THE FORM OF THEIR ALKALI SOAPS AND ONE OR MORE NONIONIC SURFACTANTS WITH THE SIMULTANEOUS ABSENCE OF ALKYL (OLIGO)GLYCOSIDES

(75) Inventors: Michael Schultz, Elmshorn (DE); Jens Treu, Norderstedt (DE)

(73) Assignee: Beiersdorf AG, Hamburg (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/901,356

(22) Filed: Jul. 9, 2001

(65) Prior Publication Data

US 2002/0037818 A1 Mar. 28, 2002

(30) Foreign Application Priority Data

Jul. 20, 2000 (DE) ........................................ 100 35 211

(51) Int. Cl.[7] ................................................ A61L 7/50

(52) U.S. Cl. ....................... 510/152; 510/153; 510/155; 510/421

(58) Field of Search ................................ 510/141, 152, 510/153, 155, 156

(56) References Cited

U.S. PATENT DOCUMENTS 5,703,026 A * 12/1997 Setser et al. ................ 510/152
5,994,281 A * 11/1999 He et al. .................... 510/152

FOREIGN PATENT DOCUMENTS

| | | |
|---|---|---|
| EP | 0 312 278 A2 | 4/1989 |
| GB | 2 317 396 A | 3/1998 |
| WO | WO 98/05752 | 2/1998 |
| WO | WO 98/55581 | 12/1998 |

* cited by examiner

*Primary Examiner*—Necholus Ogden
(74) *Attorney, Agent, or Firm*—Norris McLaughlin & Marcus

(57) ABSTRACT

Shaped soap product comprising talc, one or more fatty acids having 12–22 carbon atoms in the form of their alkali soaps and one or more nonionic surfactants with the simultaneous absence of alkyl (oligo)glycosides.

11 Claims, No Drawings

SHAPED SOAP PRODUCT COMPRISING TALC, ONE OR MORE FATTY ACIDS IN THE FORM OF THEIR ALKALI SOAPS AND ONE OR MORE NONIONIC SURFACTANTS WITH THE SIMULTANEOUS ABSENCE OF ALKYL (OLIGO)GLYCOSIDES

DESCRIPTION

Shaped soap product comprising talc, one or more fatty acids in the form of their alkali soaps and one or more nonionic surfactants with the simultaneous absence of alkyl (oligo)glycosides The present invention relates to cosmetic cleansing agents in the form of shaped soap products. Such agents are known per se. They are essentially surface-active substances or substance mixtures supplied to the consumer in various preparations. The invention relates in particular to bar soaps with improved smoothness and increased ability to disperse lime soap as a result of a content of talc and one or more nonionic surfactants and the simultaneous absence of alkyl (oligo)glycosides.

Surface-active substances—the most well-known being the alkali metal salts of higher fatty acids, i.e. the classical "soaps"—are amphiphilic substances which can emulsify the organic nonpolar substances in water.

These substances not only flush dirt from the skin and hair, they irritate skin and mucous membranes to a greater or lesser extent depending on the choice of surfactant or surfactant mixture. Although a large number of very mild surfactants is available, the surfactants of the prior art, however, are either mild, but cleanse poorly, or they cleanse well but irritate skin or mucous membranes.

Even simple bathing in water without the addition of surfactants will initially cause the horny layer of the skin to swell, the degree of this swelling depending, for example, on the bathing time and temperature. Water-soluble substances, e.g. water-soluble constituents of dirt, but also substances endogenous to the skin which are responsible for the water-binding capacity of the horny layer, are washed off or out at the same time. In addition, as a result of surface-active substances which are endogenous to the skin, skin fats are also dissolved and washed out to a certain extent. After the initial swelling, this causes a subsequent significant drying-out of the skin, which may be further intensified by washing-active additives.

The aim was therefore to remedy these shortcomings.

In healthy skin, these processes are generally of no consequence since the protective mechanisms of the skin can readily compensate for such slight disturbances to the upper layers of the skin. However, even in the case of nonpathological deviations from the norm, e.g. as a result of environmentally-induced wear damage or irritation, photodamage, aging skin etc., the protective mechanism of the surface of the skin is impaired. In some circumstances it is then no longer able to fulfil its role by itself and has to be regenerated by external measures. An object of the present invention was therefore to remedy this deficit of the prior art.

In body cleansing, a large role is played by bar soaps which are prepared nowadays on an industrial scale by continuous saponification of free fatty acids with alkalis, concentration of the base soap and spray drying. In this connection, a distinction is made between real alkali soaps, which comprise exclusively fatty acid salts and optionally also free fatty acids, and "Combibars", bar soaps which, in addition to fatty acid salts, also have further synthetic surfactants, usually fatty alcohol ether sulfates or fatty acid isethionates. In contrast, a special position is adopted by syndet bar soaps, "Syndet bars" which, apart from impurities, are free from fatty acid salts and comprise exclusively synthetic surfactants.

In Germany alone several million bar soaps are sold annually for body hygiene. Market requirements for these mass consumer articles are, however, becoming ever higher: bar soaps must not only cleanse the skin, but must also care for it, i.e. prevent drying-out, refat and offer protection against external influences. Naturally, it is expected that the soap is tolerated by the skin to a certain extent, but should nevertheless produce as large an amount of and as creamy a lather as possible during use and effect a pleasant feel on the skin. In this connection, manufacturers of bar soap are continually searching for new ingredients which take into account this increased profile of requirements.

A distinction is made between solid, mostly bar-shaped soaps, and liquid soaps. The main constituents are the alkali metal salts of the fatty acids of natural oils and fats, preferably of chain lengths $C_{12}$–$C_{18}$. Since lauric acid soaps lather particularly well, the launc acid-rich coconut and palm kernel oils are preferred raw materials for the manufacture of fine soaps. The sodium salts of the fatty acid mixtures are solid, and the potassium salts are soft-pasty. For the saponification, the diluted sodium or potassium hydroxide solution is added to the fatty raw materials in a stoichiometric ratio such that an alkali excess of at most 0.05% is present in the finished soap. Nowadays, these soaps are often not manufactured directly from the fats, but from the fatty acids obtained by cleavage of fats.

Customary soap additives are fatty acids, fatty alcohols, lanolin, lecithin, vegetable oils, partial glycerides and other fat-like substances for the refatting of cleansed skin, antioxidants, such as ascorbyl palmitate or tocopherol for preventing autoxidation of the soap (rancidity), complexing agents, such as nitrilotriacetate, for the binding of heavy metal traces which could catalyze autoxidative deterioration, perfume oils for achieving the desired scent notes, dyes for coloring the soap bars and, if desired, special additives.

The most important types of fine soaps are:

- toilet soaps containing 20–50% of coconut oil in the fatty mixture, up to 5% refatting fraction 0.5–2% of perfume oil, these make up the largest share of fine soaps;
- luxury soaps containing up to 5% of particularly expensive perfume oils;
- deodorant soaps containing additives of deodorizing active ingredient, such as, for example, 3,4,4'-trichlorocarbanilide (Triclocarban);
- cream soaps with particularly high fractions of refatting substances which cream the skin.
- baby soaps with good refatting and additionally care components, such as, for example, chamomile extracts, at most very weakly perfumed;
- skin protection soaps with high proportions of refatting substances and further care and protecting additives, such as, for example, proteins;
- transparent soaps with additives of glycerol, sugars etc., which prevent the crystallization of the fatty acid salts in the solidified soap melt and thus effect a transparent appearance;
- floating soaps with a density of <1, caused by small air bubbles incorporated in a controlled manner during the preparation.

soaps with abrasive additives for cleaning heavily soiled hands.

Upon washing with soap, a pH of 8–10 is established in the wash liquor. This alkalinity neutralizes the natural acid mantle of the skin (pH 5–6). Although in normal skin this acid mantle is reformed relatively quickly, in sensitive or predamaged skin irritations may result. A further disadvantage of soaps is the formation of insoluble lime soaps in hard water. These disadvantages are not present in the case of syndet soaps. These are based on synthetic anionic surfactants which can be incorporated with base substances, refatting agents and further additives to give soap-like bars. Their pH is variable within wide limits and in most cases is set to be neutral at pH 7 or adapted to the acid mantle of the skin at pH 5.5. They have excellent cleansing power, lather in every water hardness, even in sea water, the proportion of refatting additives has to be significantly higher than in normal soaps because of their intensive cleansing and degreasing action. Their disadvantage is the relatively high price.

Surfactants are amphiphilic substances which are able to dissolve organic nonpolar substances in water. As a result of their specific molecular structure having at least one hydrophilic and one hydrophobic molecular moiety, they are able to reduce the surface tension of water, wet skin, facilitate the removal and dissolution of dirt, facilitate rinsing and—if desired, control lathering.

The hydrophilic moieties of a surfactant molecule are mostly polar functional groups, for example $—COO^-$, $—OSO_3^{2-}$, $—SO_3^-$, while the hydrophobic moieties are generally nonpolar hydrocarbon radicals. Surfactants are generally classified according to the type and charge of the hydrophilic molecular moiety. In this connection, it is possible to differentiate between four groups:

anionic surfactants,
cationic surfactants,
amphoteric surfactants and
nonionic surfactants.

Anionic surfactants generally have carboxylate, sulfate or sulfonate groups as functional groups. In aqueous solution, they form negatively charged organic ions in an acidic or neutral medium. Cationic surfactants are almost exclusively characterized by the presence of a quatemary ammonium group. In aqueous solution, they form positively charged organic ions in an acidic or neutral medium. Amphoteric surfactants contain both anionic and cationic groups and behave accordingly in aqueous solution as anionic or cationic surfactants, depending on the pH. In a strongly acidic medium, they have a positive charge and in an alkaline medium they have a negative charge. By contrast, in the neutral pH range, they are zwitterionic, as the example below illustrates:

| | | |
|---|---|---|
| $RNH_2^+CH_2CH_2COOH\ X^-$ | (at pH = 2) | $X^-$ = any anion, e.g. $Cl^-$ |
| $RNH_2^+CH_2CH_2COO^-$ | (at pH = 7) | |
| $RNHCH_2CH_2COO^-$ | (at pH = 12) | $B^+$ = any cation, e.g. $Na^+$ |

Typical nonionic surfactants are polyether chains. Nonionic surfactants do not form ions in an aqueous medium.

It is known that fine soaps based on tallow and coconut fatty acids can be changed and improved in terms of their application properties by numerous additives. Although current handbooks, e.g. Geoffrey Martin: The Modem Soap and Detergent Industry, Vol. 1, (1959), chapter VI, describe inorganic fillers as extenders for soaps, it is more likely in this connection that talc is associated with a disadvantageous effect in bar soap. The addition of 5–20% talc in combibars is described in DE 196 49 896. This addition is said to improve the smoothness and the ability to disperse lime soaps.

The object of the invention was therefore to provide bar soaps which are free from the disadvantages described. In this connection, it was, in particular, also to be taken into consideration that new bar soap compositions also have to be preparable industrially, i.e. that the compositions have, for example, adequate, but not excessively high deformability and do not tend toward cracking upon drying.

In contrast to the losses to be expected from the prior art, it has surprisingly been established that with bar soaps which already contain alkyl glycosides as additive, a further improvement in the physical and performance properties, in particular the washing ability and the ability to disperse lime soaps and soap smoothness is achieved by an addition of talc.

The invention therefore provides a shaped soap product comprising talc, one or more fatty acids having 12–22 carbon atoms in the form of their alkali soaps and one or more nonionic surfactants with simultaneous absence of alkyl (oligo)glycosides.

Despite low overall contents of surface-active substances in the formulation, the cleaning performance and the development of lather remain unaffected. The feel on the skin is decisively improved upon use of this washing bar even without additional skin care substances.

In addition, the lather also has better creaminess and more volume, which was likewise not to be expected. A further advantage of this invention is that the compatibility of the washing bar is improved since the overall content of surface-active substances is reduced.

Moreover, the shaped soap products according to the invention have a particularly smooth surface following mechanical deformation. During use, they produce a creamy, stable lather. The lime soap precipitate formed in hard water remains dispersed in the water and does not lead to the gray-greasy deposits on the surface of sanitary objects.

Talc is a hydrated magnesium silicate of composition $3MgO\ •4SiO_2•H_2O$ or $Mg_3(Si_4O_{10})•(OH)_2$ or $Mg_6(OH)_4[Si_8O_{20}]$ or $Mg_{12}[Si_{16}O_{40}]$, which may, however, comprise fractions of hydrated magnesium aluminum silicate of up to 12% by weight of $Al_2O_3$, based on the overall product. Talc is a white, mostly very fine, virtually odorless to slightly earthy-smelling powder which feels greasy upon rubbing without being fat-containing. It is insoluble in water, cold acids or alkalis. Depending on the country of origin, the chemical purity of talc (based on the content of anhydrous magnesium silicate) is said to be 93–98%. Talc is used for the preparation of pharmaceutical, but primarily the preparation of cosmetic powders used for bodycare, but is also suitable for tablet manufacture as lubricant or flow agent.

The particle diameter (equivalent spherical diameter) of the talc should be in the range from 0.5–50 μm. In general, both talc grades which comprise not more than 5% by weight of particles below 1 μm and not more than 5% by weight of particles above 50 μm in size have proven useful. The fraction of particles greater than 40 μm in diameter (sieve residue) is preferably at most 2% by weight. The average particle diameter (D 50) is preferably 5–15 μm.

The content of concomitants should not constitute more than 1.6% by weight of $Fe_2O_3$, 1% by weight of CaO and 1% by weight of unbound water (drying loss at 1050° C.). The content of hydrated magnesium aluminum silicate can be up to 60% by weight, calculated as $Al_2O_3$, up to 12% by weight.

According to the invention, the shaped soap products advantageously comprise 1–20% by weight of talc.

According to the invention, the shaped soap products advantageously comprise 20–50% by weight of nonionic surfactants.

According to the invention, the shaped soap products (or combibars) optionally advantageously likewise comprise 5–40% by weight of a base soap, for example one whose soap constituents are composed of sodium tallowate, sodium cocoate and sodium palm kernel fatty acid salt.

Moreover, the shaped soap products according to the invention advantageously comprise water in an amount of 5–35% by weight. The water content is on the one hand determined by the preparation process, and on the other hand exerts a favorable effect on the use properties of the soap.

The fatty acids used for the preparation of the base soap are the linear fatty acids having 12 to 22 carbon atoms, e.g. lauric acid, myristic acid, palmitic acid, stearic acid, arachidic acid and behenic acid, but also the unsaturated fatty acids, e.g. palmitoleic-, oleic, linoleic, linolenic, arachidonic and erucic acid. Preference is given to using technical-grade mixtures, as are obtainable from vegetable and animal fats and oils, e.g. coconut oil fatty acid and tallow fatty acid. Particular preference is given to using mixtures of coconut and tallow fatty acid cuts, in particular a mixture of 50–80% by weight of $C_{16}$–$C_{18}$-tallow fatty acid and 20–50% by weight of $C_{12}$–$C_{14}$-coconut fatty acid.

The fatty acids are used in the form of their alkali soaps, usually as sodium soaps. However, the soaps can also be produced from the fats and oils directly by saponification (hydrolysis) with sodium hydroxide solution and removal of the glycerol. The shaped soap products according to the invention preferably comprise an additional content of 5–30% by weight of free fatty acids having 12–22 carbon atoms. These may be identical to the fatty acids of the base soap and are incorporated into the base soap by an appropriate deficit of alkali during the saponification. However, the free fatty acids are preferably metered in after saponifaction and after concentration, before drying.

Nonionic surfactants to be used advantageously are

1. Alcohols,
2. Alkanolamides, such as cocamides MEA/DEA/MIPA,
3. Amine oxides, such as cocamidopropylamine oxide,
4. Esters formed by esterification of carboxylic acids with ethylene oxide, glycerol, sorbitol or other alcohols,
5. Ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside.
6. Sucrose esters, sucrose ethers
7. Polyglycerol esters, diglycerol esters, monoglycerol esters
8. Methylglucose esters, esters of hydroxy acids.

In addition to the nonionic surfactants, the shaped soap products according to the invention may also further comprise as constituents cationic, anionic and/or amphoteric or zwitterionic surfactants.

Anionic surfactants to be used advantageously are Acylamino acids (and salts thereof), such as 1. Acyl glutamates, for example sodium acyl glutamate, di-TEA-palmitoyl aspartate and sodium caprylic/capric glutamate,
2. Acylpeptides, for example palmitoyl-hydrolyzed milk protein, sodium cocoyl-hydrolyzed soya protein and sodium/potassium cocoyl-hydrolyzed collagen,
3. Sarcosinates, for example myristoyl sarcosinate, TEA-lauroyl sarcosinate, sodium lauroyl sarcosinate and sodium cocoyl sarcosinate,
4. Taurates, for example sodium lauroyl taurate and sodium methylcocoyl taurate,
5. Acyl lactylates, lauroyl lactylate, caproyl lactylate,
6. Alaninates Carboxylic acids and derivatives, such as 1. Carboxylic acids, for example lauric acid, aluminum stearate, magnesium alkanolate and zinc undecylenate,
2. Ester carboxylic acids, for example calcium stearoyl lactylate, laureth-6 citrate and sodium PEG-4 lauramide carboxylate,
3. Ether carboxylic acids, for example sodium laureth-13 carboxylate and sodium PEG-6 cocoamide carboxylate, Phosphoric esters and salts, such as, for example, DEA-oleth-10 phosphate and dilaureth-4 phosphate, Sulfonic acids and salts, such as 1. Acyl isethionates, e.g. sodium/ammonium cocoyl isethionate,
2. Alkylarylsulfonates,
3. Alkylsulfonates, for example sodium cocomonoglyceride sulfate, sodium $C_{12-14}$-olefin-sulfonate, sodium lauryl sulfoacetate and magnesium PEG-3 cocamide sulfate,
4. Sulfosuccinates, for example dioctyl sodium sulfosuccinate, disodium laureth sulfosuccinate, disodium lauryl sulfosuccinate and disodium undecylenamido-MEA sulfosuccinate and Sulfuric esters, such as 1. Alkyl ether sulfates, for example sodium, ammonium, magnesium, MIPA, TIPA laureth sulfate, sodium myreth sulfate and sodium $C_{12-13}$-pareth sulfate,
2. Alkyl sulfate, for example sodium, ammonium and TEA lauryl sulfate.

Amphoteric surfactants for use advantageously are

1. Acyl/dialkylethylenediamine, for example sodium acyl amphoacetate, disodium acyl amphodipropionate, disodium alkyl amphodiacetate, sodium acyl amphohydroxy-propylsulfonate, disodium acyl amphodiacetate and sodium acyl amphopropionate,
2. N-alkylamino acids, for example aminopropylalkylglutamide, alkylaminopropionic acid, sodium alkylimidodipropionate and lauroamphocarboxyglycinate.

Cationic surfactants to be used advantageously are

1. Alkylamines,
2. Alkylimidazoles,
3. Ethoxylated amines,
4. Quatemary surfactants and
5. Ester quats Quatemary surfactants contain at least one N atom bonded covalently to 4 alkyl and/or aryl groups. This leads, irrespective of the pH, to a positive charge. Advantageous quaternary surfactants are alkylbetaine, alkylaminopropylbetaine and alkylamidopropylhydroxysultaine. For the purposes of the present invention, cationic surfactants may also preferably be chosen from the group of quaternary ammonium compounds, in particular benzyltrialkyl-ammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethyl-ammonium chlorides or bromides, alkylamidoethyltrimethylammonium ether sulfates, alkyl-pyridinium salts, for example lauryl- or cetylpyridinium chloride, imidazoline derivatives and compounds with cationic character, such as amine oxides, for example alkyldimethylamine oxide or alkylaminoethyidimethylamine oxide. Cetyltrimethylammonium salts in particular are to be used advantageously.

A feature of the invention is the absence of alkyl (oligo) glycosides. Alkyl (oligo)glycosides are known, commercially available, nonionogenic surfactants which are available by relevant methods of organic chemistry and correspond to the formula $R^1$-$O(G)_x$, in which $R^1$ is a primary $C_{12}$–$C_{16}$ alkyl group and $(G)_x$ is an oligoglycoside radical whose degree of oligomerization x=1 to 2. By way of representation of the extensive literature, reference may be made here to EP-A-0 301 298 and WO-A-90/3977. The alkyl (oligo)glycosides can be derived from aldoses or ketoses having 5 or 6 carbon atoms. Because of its ready availability, alkyl (oligo)glucosides derived from glucose are mainly prepared on an industrial scale. The absence of these substances means that at worst they must be present as impurities in the mass which forms the basis of the combibar according to the invention, and in any case must be less than 1% by weight.

The shaped soap products according to the invention can comprise, as further auxiliaries and additives, oily substances (refatting agents), emulsifiers, superfatting agents, fats, waxes, stabilizers, cationic polymers, silicone compounds, pigments, biogenic active ingredients, preservatives, dyes and fragrances.

Examples of refatting agents which may be used advantageously according to the invention are:

1. long-chain alcohols, e.g. lanolin, cetyl alcohol
2. mono- and diglycerides or the corresponding glycol esters
3. mono-, di- and triglycerides of a vegetable origin e.g. almond oil
4. hydrogenated fats
5. Vaseline
6. waxes Also suitable as refatting agents are, for example, oily substances, such as, for example, Guerbet alcohols based on fatty alcohols having 6 to 18, preferably 8 to 10, carbon atoms, esters of linear $C_6$–$C_{20}$-fatty acids with linear $C_6$–$C_{20}$-fatty alcohols, esters of branched $C_6$–$C_{13}$-carboxylic acids with linear $C_6$–$C_{20}$-fatty alcohols, esters of linear $C_6$–$C_{18}$-fatty acids with branched alcohols, in particular 2-ethylhexanol, esters of linear and/or branched fatty acids with polyhydric alcohols (such as, for example, dimerdiol or trimerdiol) and/or Guerbet alcohols, triglycerides based on $C_6$–$C_{10}$-fatty acids, vegetable oils, branched primary alcohols, substituted cyclohexanes, Guerbet carbonates, dialkyl ethers and/or aliphatic or naphthenic hydrocarbons.

Emulsifiers and coemulsifiers which may be used are nonionogenic, ampholytic and/or zwitterionic interface-active compounds which are distinguished by a lipophilic, preferably linear, alkyl or alkenyl group and at least one hydrophilic group. This hydrophilic group can either be an ionogenic group or a nonionogenic group.

Nonionogenic emulsifiers comprise, as a hydrophilic group, for example, a polyol group, a polyalkylene glycol ether group or a combination of polyol and polyglycol ether group. Preference is given to those agents which comprise, as O/W emulsifiers, nonionogenic surfactants from at least one of the following groups: (a1) addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group; (a2) $C_{12/18}$-fatty acid mono- and diesters of addition products of from 1 to 30 mol of ethylene oxide onto glycerol; (a3) glycerol mono- and diesters and sorbitan mono- and diesters of saturated and unsaturated fatty acids having 6 to 22 carbon atoms and their ethylene oxide addition products and (a4) addition products of from 15 to 60 mol of ethylene oxide onto castor oil and/or hydrogenated castor oil; (a5) polyol and, in particular, polyglycerol esters, such as, for example, polyglycerol polyricinoleate or polyglycerol poly-12-hydroxystearate. Also suitable are mixtures of compounds from two or more of these classes of substance. The addition products of ethylene oxide and/or of propylene oxide onto fatty alcohols, fatty acids, alkylphenols, glycerol mono- and diesters, and sorbitan mono- and diesters of fatty acids or onto castor oil are known, commercially available products. These are homolog mixtures whose average degree of alkoxylation corresponds to the ratio of the quantitative amounts of ethylene oxide and/or propylene oxide and substrate with which the addition reaction is carried out. $C_{12/14}$-fatty acid mono- and diesters of addition products of ethylene oxide onto glycerol are known from DE-20 24 051 as refatting agents for cosmetic preparations.

Suitable as W/O emulsifiers are: (b1) addition products of from 2 to 15 mol of ethylene oxide onto castor oil and/or hydrogenated castor oil; (b2) partial esters based on linear, branched, unsaturated or saturated $C_{12/22}$-fatty acids, ricinoleic acid, and 12-hydroxystearic acid and glycerol, polyglycerol, pentaerythritol, dipentaerythritol, sugar alcohols (e.g. sorbitol) and polyglucosides (e.g. cellulose); (b3) trialkyl phosphates; (b4) wool wax alcohols; (b5) polysiloxane-polyalkyl-polyether copolymers and corresponding derivatives; (b6) mixed esters of pentaerythritol, fatty acids, citric acid and fatty alcohol according to German patent 11 65 574, and (b7) polyalkylene glycols.

Suitable cationic polymers are, for example, cationic cellulose derivatives, cationic starch, copolymers of diallylammonium salts and acrylamides, quatemized vinylpyrrolidone/vinylimidazole polymers, such as, for example, Luviquat TM (BASF AG), condensation products of polyglycols and amines, quatemized collagen polypeptides, such as, for example, "lauryldimonium hydroxypropyl hydrolyzed collagen" (Lamequat TM L, Grünau GmbH) or "lauryidimonium hydroxypropyl hydroxylated wheat protein" (Gluadin TM WQ, Grünau GmbH), polyethyleneimine, cationic silicone polymers, such as, for example, amidomethicones or Dow Coming, Dow Coming Co./US, copolymers of adipic acid and dimethylaminohydroxypropyidiethylenetriamine (Cartaretine TM, Sandoz/CH), polyaminopolyamides as described, for example, in FR 22 52 840-A, and crosslinked water-soluble polymers thereof, cationic chitin derivatives, such as, for example, quatemized chitosan, optionally in microcrystalline distribution, cationic guar gum, such as, for example, Jaguar TM CBS, Jaguar TM C-17, Jaguar TM C-16 (Celanese) or Cosmedia Guar TM C 261 (Henkel KGaA), quatemized ammonium salt polymers, such as, for example, Mirapol TM A-15, Mirapol TM AD-1, Mirapol TM AZ-1 from Miranol/US. Suitable silicone compounds are, for example, dimethylpolysiloxanes, methylphenylpolysiloxanes, cyclic silicones, and amino-, fatty acid-, alcohol-, polyether-, epoxy-, fluorine- and/or alkyl-modified silicone compounds. Superfatting agents which may be used are substances such as, for example, polyethoxylated lanolin derivatives, lecithin derivatives, polyol fatty acid esters, monoglycerides and fatty acid alkanolamides, the latter also serving as lather stabilizers. Typical examples of fats are glycerides, and suitable waxes are, inter alia, beeswax, paraffin wax or microcrystalline waxes, optionally in combination with hydrophilic waxes, e.g. cetylstearyl alcohol. Stabilizers which may be used are metal salts of fatty acids, such as, for example, magnesium stearate, aluminum stearate and/or zinc stearate. An example of a suitable pigment is titanium dioxide. Biogenic active ingredient is understood as meaning, for example, plant extracts and vitamin complexes. Suitable preservatives are, for example, phenoxyethanol, formaldehyde solution, parabens, pentanediol or sorbic acid. Dyes which may be used are the substances approved and suitable for cosmetic purposes, as listed, for example, in the publication "Kosmetische F ärbemittel" [Cosmetic Colorants] from the Farbstoffkommission der Deutschen Forschungsgemeinschaft [Dyes Commission of the German Research Society], Verlag Chemie, Weinheim, 1984, pp. 81–106. These dyes are usually used in concentrations of from 0.001 to 0.1% by weight, based on the total mixture. The total content of auxiliaries and additives can be 1 to 50% by weight, preferably 5 to 40% by weight, based on the agent.

Finally, the shaped soap products according to the invention can comprise fragrances and further customary auxiliaries and additives in an amount of up to 5% by weight. Suitable auxiliaries are, for example, binding agents or plasticizers. Suitable as such are, for example, glycerol, fatty acid partial glycerides or fatty alcohols having 12–22 carbon atoms.

Further auxiliaries are, for example, dyes, antimicrobial substances, deodorant active ingredients, pigments ($TiO_2$), optical brighteners and complexing agents.

The shaped soap products according to the invention can be produced in the manner customary for soaps. Firstly, a base soap with a solids content of 25–50% by weight is prepared from fatty acid mixture and sodium hydroxide solution and concentrated to a solids content of 50–70% by weight. As early as at this point it is possible to mix the talc, optionally also free fatty acid, a nonionic surfactant and a complexing agent, into this e.g. 60% strength base soap. The base soap is then further dewatered e.g. in a vacuum expansion dryer at 120° C. to 130° C. During the expansion, the soap cools spontaneously to temperatures below 60° C. and becomes solid. In the process, soap noodles with a solids content of 73–85% by weight are produced.

The further processing of this base soap then represents the formulation to give the fine soap. This takes place in a soap mixer in which a slurry of the nonionic surfactant(s) and the other auxiliaries and additives are mixed into the soap noodles. Here, the base soap noodles and the slurry of nonionic surfactant(s) and e.g. fragrances, dyes, pigments and other auxiliaries are mixed intensively in a screw mixer with perforated screens and finally discharged through a plodder and optionally passed to a bar stamper if soap bars are to be produced.

Shaped soap products for the purposes of the invention can, however, also be in the form of noodles, needles, granules, extrudates, flakes and in any other shape customary for soap products.

Alternatively to the process described, the talc can also only be incorporated into the 73–85% pure base soap during formulation. In this case, the talc powder is fed to the soap mixer by suitable dosing devices, e.g. belt weigher and vibrating feeder, at the same time as the slurry comprising the nonionic surfactants, fragrances and auxiliaries.

The soap products according to the invention are notable for a particularly smooth surface which is pleasantly noticeable in particular in the case of processing to give bar soap. During use, a rich finely-bubbled creamy lather forms. Although lime soap precipitations do form in hard water, they remain dispersed in the solution and do not deposit onto hard surfaces as greasy-gray marks or a curdy rim, but at worst precipitate out as a slight, finely divided cloudiness.

The examples below serve to illustrate the invention without limiting it.

Base soap

| | % by wt. |
|---|---|
| Sodium tallowate | 67.80 |
| Sodium cocoate/Sodium palm kernel fatty acid salts | 16.95 |
| NaCl | 0.40 |
| EDTA | 0.20 |
| Sodium etidronate | 0.09 |
| Glycerol | 2.50 |
| Water | ad 100.00 |

Example 1

| | % by wt. |
|---|---|
| Cocamidopropylamine oxide | 31.00 |
| Stearic acid | 23.00 |
| Base soap | 11.00 |
| Paraffin | 8.00 |
| Coconut fatty acids | 3.00 |
| Paraffin | 2.00 |
| Polyethylene glycol-150 | 2.00 |
| Talc | 5.00 |
| $TiO_2$ | 0.50 |
| Panthenol | 0.15 |
| Wool wax alcohol | 0.10 |
| Water | ad 100.00 |

The base soap noodles are metered with the other components into a customary soap mixer (screw mixer with perforated screen), homogenized by repeated mixing, discharged via a plodder, cut and processed to give bars in the usual manner.

What is claimed is:

1. A shaped soap product comprising talc, one or more $C_{12}$–$C_{22}$ fatty acids in the form of their alkali soaps and one or more nonionic surfactants wherein said soap product does not contain any alkyl (oligo)glycosides wherein the one or more nonionic surfactants are selected from the group consisting of alkanolamides; amine oxides; esters which are formed by esterification of carboxylic acids with ethylene oxide, glycerol sorbitol; propoxylated alcohols; ethoxylated/propoxylated esters; ethoxylated/propoxylated glycerol esters; ethoxylated/propoxylated cholesterols; ethoxylated/propoxylated triglyceride esters; ethoxylated/propoxylated lanolin; ethoxylated/propoxylated polysiloxanes; propoxylated POE ethers; sucrose esters; sucrose ethers; polyglycerol esters; diglycerol esters; monoglycerol esters; methylglucose esters and esters of hydroxy acids.

2. The soap product of claim 1, wherein the fatty acids are composed of 50–80% by weight of $C_{16}$–$C_{18}$ fatty acids and from 20–50% by weight of $C_{12}$–$C_{14}$ fatty acids.

3. The soap product of claim 1, which further comprises of 5–30% by weight of one or more $C_{12}$–$C_{22}$ fatty acid(s) not in the form of their alkali soaps.

4. The soap product of claim 1, wherein the nonionic surfactant comprises 20–50% by weight.

5. The soap product of claim 1, wherein talc comprises 1–20% by weight.

6. The soap product of claim 1, wherein the one or more $C_{12}$–$C_{22}$ fatty acids in the form of their alkali soaps comprises 5–40% by weight.

7. The soap product of claim 6, wherein the one or more $C_{12}$–$C_{22}$ fatty acids in the form of their alkali soaps is a base soap which is comprised of sodium tallowate, sodium cocoate and sodium palm kernel fatty acid salt.

8. The soap product of claim 1, which further comprises of water in an amount of 5–35% by weight.

9. The soap product of claim 1, which further comprises of up to 15% by weight of synthetic, cationic, zwitterionic or ampholytic surfactants.

10. The soap product of claim 1, wherein the alkanolamides are a cocamide MEA/DEA/MIPA.

11. The soap product of claim 1, wherein the amino oxides are a cocamidopropylamine oxide.

* * * * *

UNITED STATES PATENT AND TRADEMARK OFFICE

CERTIFICATE OF CORRECTION

PATENT NO. : 6,541,433 B2 
DATED : December 7, 1999
INVENTOR(S) : Michael Schultz and Jens Treu It is certified that error appears in the above-identified patent and that said Letters Patent is hereby corrected as shown below:

<u>Column 10,</u>
Line 57, “glycerol sorbitol” should read -- glycerol, sorbitol --

Signed and Sealed this

Ninth Day of November, 2004

JON W. DUDAS
*Director of the United States Patent and Trademark Office*